United States Patent
Lobe et al.

(10) Patent No.: US 10,179,862 B2
(45) Date of Patent: *Jan. 15, 2019

(54) OPTICALLY CLEAR BIOFOULING RESISTANT COMPOSITIONS AND METHODS FOR MARINE INSTRUMENTS

(71) Applicants: Severn Marine Technologies, LLC, Annapolis, MD (US); Mid Mountain Materials, Inc., Mercer Island, WA (US)

(72) Inventors: Henry Lobe, Annapolis, MD (US); John Knapp, Seattle, WA (US); Amulya K. Das, Everett, WA (US); Gary Moffat, Arlington, WA (US)

(73) Assignees: Severn Marine Technologies, LLC, Annapolis, MD (US); Mid-Mountain Materials, Inc., Mercer Island, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,855

(22) Filed: Jan. 6, 2017

(65) Prior Publication Data

US 2017/0114230 A1    Apr. 27, 2017

Related U.S. Application Data

(63) Continuation of application No. 12/714,129, filed on Feb. 26, 2010, now Pat. No. 9,562,163.

(60) Provisional application No. 61/155,860, filed on Feb. 26, 2009.

(51) Int. Cl.
*C09D 5/16* (2006.01)
*C09D 5/14* (2006.01)
*C09D 183/04* (2006.01)

(52) U.S. Cl.
CPC ............ *C09D 5/1675* (2013.01); *C09D 5/14* (2013.01); *C09D 5/1625* (2013.01); *C09D 5/1693* (2013.01); *C09D 183/04* (2013.01)

(58) Field of Classification Search
CPC ....... A01N 55/00; C08L 75/04; C09D 183/04; C09D 5/14; C09D 5/1625; C09D 5/1675; C09D 5/1693
See application file for complete search history.

(56) References Cited

U.S. PATENT DOCUMENTS

| | | |
|---|---|---|
| 3,744,016 A | 7/1973 | Davis |
| 4,025,693 A | 5/1977 | Milne |
| 4,701,345 A | 10/1987 | Giatras et al. |
| 4,851,009 A | 7/1989 | Pinchuk |
| 4,861,670 A | 8/1989 | Lampe et al. |
| 4,996,257 A | 2/1991 | Saito et al. |
| 5,147,725 A | 9/1992 | Pinchuk |
| 5,218,059 A | 6/1993 | Kishihara et al. |
| 5,272,012 A | 12/1993 | Opolski |
| 5,449,553 A | 9/1995 | Griffith |
| 5,571,312 A | 11/1996 | Andoe |
| 5,904,988 A | 5/1999 | Stein et al. |
| 5,958,116 A | 9/1999 | Kishihara et al. |
| 2002/0010228 A1 | 1/2002 | Simendinger |
| 2002/0189087 A1 | 12/2002 | Wilemon et al. |
| 2006/0094834 A1 | 5/2006 | Aoki et al. |
| 2006/0106157 A1 | 5/2006 | Sawant et al. |
| 2006/0115335 A1 | 5/2006 | Allen et al. |
| 2007/0021529 A1 | 1/2007 | Boudjouk |
| 2008/0138634 A1 | 6/2008 | Morris et al. |
| 2008/0166493 A1 | 7/2008 | Xiao et al. |
| 2008/0255304 A1 | 10/2008 | Nakashima |

FOREIGN PATENT DOCUMENTS

| | | |
|---|---|---|
| EP | 0 530 074 A1 | 3/1993 |
| WO | 2008/046166 A2 | 4/2008 |

OTHER PUBLICATIONS

CAS No. 68410-23-1, "Fatty acids, C18-unsatd., dimers, reaction products with polyethylenepolyamines," Chemical Book, 2008, <http://www.chemicalbook.com/ProdSupplierGWCB31213275_EN.htm> [retrieved Oct. 29, 2012], 1 page.

Communication Pursuant to Article 94(3) EPC dated Oct. 29, 2013, issued in corresponding Application No. EP 05 769 470.5, filed Jun. 30, 2005, 8 pages.

"Dow Corning® P5200 Adhesion Promoter—Clear," Material Safety Data Sheet No. 02710480, Dow Corning Corporation, Midland, Mich., rev. Jun. 30, 2004, 9 pages.

"Dow Corning® P5200 Adhesion Promoter: Construction Sealant and Primer," Product Information, Form No. 62-1117-01, Dow Corning Corporation, Midland, Mich., 2002, 2 pages.

Extended European Search Report dated May 25, 2011, issued in corresponding Application No. EP 11 155 861.5, filed Feb. 24, 2011, 8 pages.

*Primary Examiner* — Matthew P Coughlin
*Assistant Examiner* — Thurman M Wheeler
(74) *Attorney, Agent, or Firm* — Christensen O'Connor Johnson Kindness PLLC

(57) ABSTRACT

An optically clear biofouling resistant coating compositions specially formulated for very high light transmission and more particularly coating compositions which can be applied to marine instruments and sensors. The compositions provide a biofouling resistant coating on the surface of the marine instruments and sensors which prevents underwater organisms from adhering and growing on the surfaces of the structures over a long period of time.

18 Claims, 1 Drawing Sheet

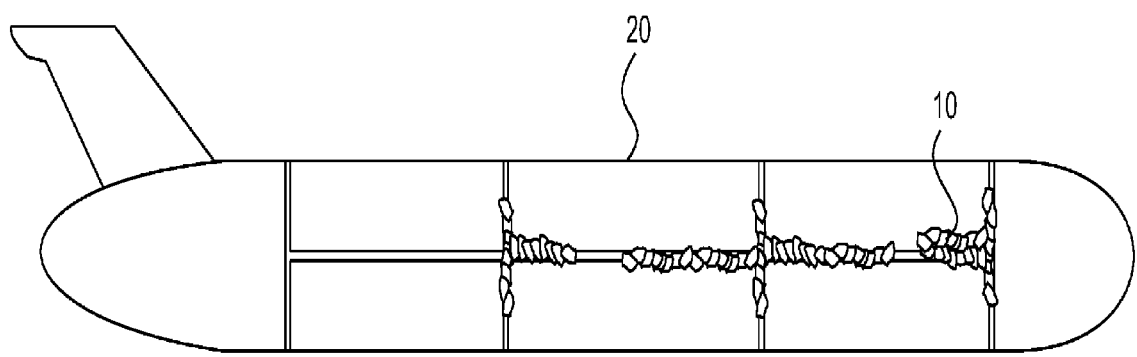

OPTICALLY CLEAR BIOFOULING RESISTANT COMPOSITIONS AND METHODS FOR MARINE INSTRUMENTS

CROSS-REFERENCES TO RELATED APPLICATIONS

This application is a continuation of U.S. application Ser. No. 12/714,129, filed on Feb. 26, 2010, which claims the benefit of Provisional Application No. 61/155,860, filed on Feb. 26, 2009, the disclosures of which are hereby incorporated by reference in their entirety.

BACKGROUND

Field of the Invention

The present invention relates to optically clear biofouling resistant coating organosiloxane compositions specially formulated for very high light transmission, and more particularly to coating compositions which can be applied to marine instruments and sensors. The compositions provide a biofouling resistant coating on the surface of the marine instruments and sensors which prevents underwater organisms from adhering and growing on the surfaces of the structures over a long period of time.

Description of the Prior Art

A large number of organisms such as barnacles, bacterial slimes, ascidians, serupulas, fresh- and salt-water mussels, polyzoan, green algae, sea lettuce and the like live in the waters of the sea, rivers, lakes and swamps. These plants and animals cause various types of damages, and particularly adhere to and degrade the performance of marine instruments and sensors.

The biofouling of marine and other aquatic instrumentation is a long-felt and well-established problem by those in industry, science and resource management, as biofouling inhibits the performance of marine instrumentation, thereby adversely affecting the data acquired as well as adding to the cost of maintaining the instruments. Problems due to biofouling of marine instrumentation have been occurring for many decades and continue to be a major factor inhibiting the effective use of submerged instruments.

Biofouling on the marine instrument housing causes messy handling of the instrument upon retrieval; increases the surface area of the housing thereby making the instrument more susceptible to forces imparted on it from current, waves or other moving water; increases the weight of the instrument both in and out of the water; increases personnel time to clean with an associated increase in operation and maintenance cost the biofouling that attaches to the surface area of the housing has a tendency to migrate towards the sensor area.

Additionally, the biofouling on the sensor elements can attenuate sensor signals, disrupt critical spacing between conductor elements, disable optical devices due to blockage of light transmission through their elements; block open ports of pressure or sensing chambers, clogs open flow cylinders of some sensors and some biofouling organisms such as barnacles can bore into the transducer elements, thereby damaging them.

Biofouling of marine instruments comprising a housing and sensor element continues to be a persistent problem. Prior attempts to address the problems associated with biofouling of sensor elements have involved using, mechanical wipers to remove biological material from the sensor elements; various grease types which work through ablative processes or through the incorporation of active agents such as pepper extracts or other traditional metal biocides, tributyl tin tablets that sterilize the local sensing area or chamber contained sensor area, using traditional paints containing active biocides, sensor encapsulation boxes that prevent light from contacting the sensor element when it is not in use and thereby prevent or limit biofouling, chlorine systems that often use electrolysis to generate chlorines from seawater, various chemical treatments that are injected into a closed chamber system and using copper mounting plates for sensor components.

Other prior attempts to address the problems associated with biofouling of housing elements include the use of various grease types which work through ablative processes or through the incorporation of active agents such as pepper extracts or other traditional metal biocides, use of traditional paints containing active biocides, or various types of tapes that are wrapped on the housings and then removed when the instrument is retrieved, thus removing the biofouling.

Prior art techniques have obvious limitations. For instance, use of grease for preventing biofouling of instrument housing may be initially effective; its effectiveness diminishes over time as the greases need to be periodically reapplied as the grease is washed off. Furthermore, greases may have adverse environmental effects as they are in some cases toxic to non-biofouling marine life and to workers handling and maintaining the marine instruments. On the other hand, paints or any opaque coating will not work on optical sensors as they will disrupt light transmission in the same manner that biofouling itself does. Additionally, metal biocide released from various paints or greases cannot work with electrode or electromagnetic sensor elements as they will disrupt the generated signal. Mechanical wipers have proven to improve the duration that optical instruments can be deployed. Fouling does however occur and the mechanical systems use a significant amount of battery power for those devices that are battery powered. Furthermore, paints containing active biocides or other biocide applications lose their efficacy over time. The copper mounting plates noted have moderate effectiveness in reducing biofouling accumulation. The use of tapes on instrument housing does not reduce the degree of biofouling but simply protects the instrument housing and allows the user to clean the instrument by removing the tape rather than scraping the instrument.

Where marine instruments have been coated with opaque biofouling resistant material, the coating occludes the identity of the instrument causing manufacturers to loose their identifying look and branding; serial numbers and other identification markings.

In order to solve the above problems, various coating compositions have previously been proposed. For example, U.S. Pat. Nos. 4,025,693 and 5,218,059, 5,958,116 disclose coating compositions which are prepared using a silicone rubber alone or as a mixture with silicone oil. US 20080166493 disclose silicone based coating compositions containing ceramic nanoparticles. US 20080255304 relate to integrally molded body of silicone resin and silicone rubber but does not teach an antibiofouling composition. Prior art does not provide optically clear silicones nor address the issue of poor silicone adhesion to a wide variety of marine instrument surfaces, particularly adhesion promotion in a manner that does not interfere with light transmission. Hence, there is need for biofouling resistant coating compositions specially formulated for very high light transmission without impeding the effectiveness of the submerged instruments.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides an optically clear biofouling resistant organosiloxane-based coating composition and method for marine instruments comprising housing and sensor elements, said composition capable of forming a coating having excellent biofouling resistant properties, adhesion to the substrate and coating durability. As used in this description, instrument housing also includes moveable and fixed platforms that contain undersea instruments such as Autonomous Undersea Vehicles (AUV), Gliders and Buoys. As used in this specification, optical clarity refers to a coating composition that is optically transparent (>70% light transmission between 400 and 800 nm), preferably greater than 90% light transmission between 400 and 800 nm and most preferably greater than 95% light transmission between 400 and 800 nm. Preferably the refractive index of the composition is above 1.40.

The biofouling resistant coating of the invention is the reaction product of a composition specially formulated for very high light transmission comprising a curably reactive organosiloxane, preferably polydimethylsiloxane, an organosilane cross linking agent, and optionally a reinforcing silica or silica resin, where appropriate, a metal catalyst, and where appropriate adhesion promoters, primers and substrate surface treatments such as corona.

It is one object of the present invention to provide an optically clear biofouling resistant coating composition for marine instruments. As used in this specification, marine instruments encompass instruments intended to be used in a submerged environment for extended periods of time. Such instruments generally comprise a waterproof and pressure proof housing which contains a sensor(s) element(s) that is exposed to the ambient water. The housing typically contains electronics, batteries, data storage and a means to mount the sensor element. The sensor element is typically an acoustic transducer, optical sensor, electromagnetic device, electrode device, strain gage device or sensing chamber that uses any number of chemical, optical or other measurement techniques.

It is another object of the present invention to provide an optically clear biofouling resistant coating composition for the waterproof pressure housings of marine instruments, said water proof housings made of materials including but not limited to aluminum, titanium, stainless steel, copper nickel, glass, polyurethane, poly vinyl chloride, ceramic, poly acetyl, fiberglass reinforced plastic, carbon fiber reinforced plastic, other thermo plastics, other thermo sets.

It is another object of the present invention to provide an optically clear biofouling resistant coating composition for the exposed sensor elements of marine instruments; said sensors made of materials including stainless steel, glass, epoxy, polyurethane, titanium, other thermo plastic plastics, other thermo set plastics, and ceramics.

It is yet another object of the present invention to provide an optically clear biofouling resistant coating composition for acoustic sensors which generally measure ocean current, produce sea bottom imagery, produce mid water imagery, measure small and large aquatic life, measure suspended sediments or particles in water or produce imagery of man made devises such as ship hulls, mines, shipwrecks and submerged structures of various types.

It is yet another object of the present invention to provide an optically clear biofouling resistant coating composition for optical sensors which generally measure: dissolved oxygen, florescence, chlorophyll, turbidity, ph and bioluminescence.

It is yet another object of the present invention to provide an optically clear biofouling resistant coating composition for electrode or electromagnetic sensors which generally measure: conductivity, temperature, and water flow.

It is yet another object of the present invention to provide an optically clear biofouling resistant coating composition for strain gauge devices which generally measure pressure.

The present invention also provides a method of coating marine instruments comprising housing and sensor elements, said method capable of forming an optically clear biofouling resistant coating having excellent biofouling resistant properties, a high degree of coating adhesion to the substrate as well as a high degree of coating durability.

One object of the invention provides a method of coating marine instruments which generally comprise a waterproof and pressure proof housing which contains a sensor(s) element(s) that is exposed to the ambient water, said method capable of forming an optically clear biofouling resistant coating having excellent long term biofouling resistant properties, a high degree of coating adhesion to the substrate as well as a high degree of coating durability.

It is yet another object of the present invention to provide a method of coating the waterproof pressure housings of marine instruments, said water proof housings made of materials including but not limited to aluminum, titanium, stainless steel, copper nickel, glass, polyurethane, poly vinyl chloride, ceramic, poly acetyl, fiberglass reinforced plastic, carbon fiber reinforced plastic, other thermo plastics, other thermo sets, said method capable of forming an optically clear biofouling resistant coating having excellent biofouling resistant properties and biofouling resistant durability.

It is another object of the present invention to provide a method of coating the exposed sensor elements of marine instruments; said sensors made of materials including stainless steel, glass, epoxy, polyurethane, titanium, other thermo plastic plastics, other thermo set plastics, and ceramics said method capable of forming an optically clear biofouling resistant coating having good adhesion to the substrate and coating durability.

It is yet another object of the present invention to provide a method of coating acoustic sensors, optical sensors, electromagnetic sensors, strain gauge, said method capable of forming an optically clear biofouling resistant coating having excellent biofouling resistant properties and biofouling resistant durability.

One embodiment of the invention is one in which the composition and method of the present invention is used in conjunction with other biofouling resistant methodologies known in the art. For instance, in conjunction with mechanical wiper system, the composition and method of the present invention will result in a more effective cleaning of the coated sensor and/or housing. In another embodiment, the composition of the present invention further comprises organic compounds having antibiofoulant properties selected from compounds consisting of algaecides, herbicides, bactericides, and pesticides as well natural product antibiofoulants such as capsaicin and zosteric acid.

Mixtures of two or more antibiofoulants can be used. Preferred anti biofoulants are those compounds that are stable at processing conditions and that do not excessively decrease transmission of light through the cured composition or damage the compositions' physical and mechanical properties to any appreciable extent.

In another embodiment, to enhance adhesion of the coating material and increase biofouling resistant durability, a silicone based primer may be applied to the sensor or instrument housing to be coated with the composition of the present invention. In yet another embodiment, the instrument housing can be corona treated to promote adhesion of the coating.

In yet another embodiment, to enhance adhesion of the coating material and increase biofouling resistant durability, a clear paint barrier such as epoxy or polyurethane may be applied to the instrument housing or sensor to serve as a tie coat in order to provide barrier substrate for the composition of the present invention to attach. The barrier will also prevent any constituents from the instrument housing or sensor from disrupting the adhesion of the silicone coating.

The composition of the present invention may be a two part heat-cured system or it may be a one part system that is cured at room temperatures or accelerated temperatures.

The present invention also provides an optically clear biofouling resistant coating composition and method for marine instruments comprising housing and sensor elements, said composition capable of forming a coating having excellent long term biofouling resistant properties, coating durability and good adhesion to the substrate, said method and composition being environmentally friendly and safe to handle.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates biofouling in o-ring jointed seams of a multi-component marine instrument housing.

DETAILED DESCRIPTION

The present invention will be more fully understood by reference to the following description and examples. Variations and modifications of the embodiments of the invention can be substituted without departing from the principles of the invention, as will be evident to those skilled in the art.

The marine instruments which can be coated by the present invention can be any of the known marine instruments and sensors which are likely to be used underwater for extended periods of time. These include, for example, electroacoustic, sonic and optical apparatus for marine purposes; survey, shipping, signal, measurement and monitoring apparatus for underwater applications; acoustic echosounders for range measurement in water; temperature, sediment transport, chlorophyll, florescence, turbidity, acoustic fish-finding apparatus, multihydrophone listening devices, acoustic locating and control apparatus; apparatus for underwater telephony; apparatus for pollutant detection and pollutant analysis in seas and in inland waters; sonar equipments and parts thereof; command and weapons control systems on underwater vessels, mainly consisting of surveillance sensors for sea areas, acoustic homing heads, underwater propelled guided vehicles; underwater locating apparatus; submerged navigation and control systems for ships; surveillance systems for inland waterways, sea waterways, harbors and coasts, apparatus for iceberg detection; survey systems for waters and parts of such systems, fanbeam echosounders, underwater recording apparatus and evaluation apparatus; hydrophone machines and apparatus, namely, hydrophones and underwater recording or listening instruments; underwater surveying apparatus and instruments, namely, surveying apparatus and instruments in the field of processing, acquisition and interpretation of seismic data for use in exploration and exploitation of the hydrocarbon deposits in underwater surfaces specifically seismic exploration machines and apparatus; tools with underwater acoustic sensors, tools with underwater vibration sensors and tools with underwater acceleration sensors, namely, seismic exploration machines, seismological instruments, seismometers; underwater scientific apparatus and instruments, namely, scientific apparatus and instruments in the field of processing, acquisition and interpretation of geophysical data for use in exploration and exploitation of the aquatic subsoil and for processing and interpretation of seismic data for searching out and exploitation of hydrocarbon deposits.

The above marine instruments comprising a housing and sensor elements can be made of nearly any material which is suitable for the application. This includes, for example, plastics, elastomers, metals and the like. Specific materials for the sensor elements also include but are not limited to polyvinylchlorides (PVC), polycarbonates (PC), polyurethanes (PU), polypropylenes (PP), polyethylenes (PE), polyesters, polymethylmethacrylate (PMMA), hydroxy ethylmethacrylate, N-vinyl pyrrolidones, fluorinated polymers such as polytetrafluoroethylene, polyamides, polystyrenes, copolymers or mixtures of the above polymers.

The marine instrument made of the above materials is coated with the optically clear biofouling resistant coating of the invention. As used in this description, "biofouling resistant," "fouling release," or "antibiofouling" are used interchangeably to refer to the process of preventing or reducing the accumulation of fouling organism on marine instrument housing and sensor elements using the methods and composition of the present invention. The entire device may be coated with this coating or, alternatively, just that portion of the device that is submerged under water can be coated. It is understood by one of skill in the art that the different embodiments of a particular marine instrument may be coated with different biofouling resistant coating compositions most suited for its constituent materials.

The biofouling resistant coating of the invention is the reaction product of a composition specially formulated for very high light transmission comprising a curably reactive organopolysiloxane having reactive functional groups and silicon bonded organic groups, a cross linking agent, optionally a filler or a reinforcing silica, optionally an adhesion promoter, and optionally a metal catalyst. Preferred silicon bonded organic group include a methyl group, an ethyl group, a vinyl group, a haloalkyl group, and a phenyl group. The specific curing mechanism can vary widely, and depends on the nature of the functional groups, for example, hydrolyzation, dealcoholyzation, deacetification, dehydroxyamination and the like. In a preferred embodiment, at least one terminal end of the organopolysiloxane polymer has at a terminal reactive group; preferably the terminal reactive group is a hydroxyl group, an alkoxy group, an aryloxy group, an amino group, an amido group, a halogen, or a vinyl group.

The curably reactive organopolysiloxane is preferably a reactive polydimethylsiloxane (PDMS) $(H_3C)_3SiO[Si(CH_3)_2 O]_nSi(CH_3)_3$, where n is the number of repeating monomer [SiO(CH₃)₂] units, said reactive PDMS being preferably condensation or addition/heat cured.

Condensation cured materials are room temperature vulcanizing resins (RTVs) which use ambient moisture for curing. Condensation cures can also be of the neutral type that can be cured by either alkoxy or oxine promoter released from the material. They can be commercially available as one part systems. Condensation cured materials can also be two part systems. These use what is typically a metal catalyst in conjunction with the ambient moisture. These materials are not susceptible to premature curing by exposure to moisture. These material types are typically alkoxy cross link promoter released. Addition cure materials use platinum as the catalyst. They are designed to be heat cured materials but are sometimes reformulated to cure at room temperatures. This type of material has no by products. Addition cure materials tend to have better optical clarity than condensation cured organopolysiloxane. As used in this specification, optically clear coating refers to fouling release coating of the present invention having a high refractive index and light transmission of greater than 50%.

In one embodiment, the reactive organopolysiloxane can be nearly any which reacts with acetoxysilane cross linking agent to cure and form the optically clear biofouling resistant coating. Such organopolysiloxanes generally have reactive groups such as hydrogen, hydroxyl, alkoxy or alkoxy bound to silicon in the polymer.

As such, the reactive organopolysiloxanes generally have siloxane units of the general structure:

$$R_xR^1SiO_{(3-x)} \qquad \text{I}$$

in which each R represents a monovalent hydrocarbon group having up to 20 carbon atoms such as an alkyl (e.g., methyl, ethyl, propyl or butyl) or phenyl groups, x is 1 or 2 and $R^1$ represents a hydrogen, a hydroxyl (OH) group or an alkoxy group (OR) such as methoxy, ethoxy, propenyloxy and the like. Preferably, R is methyl and $R^1$ is hydroxyl.

The reactive organopolysiloxanes can, and preferably does, also have other units such as, for example, units of the general structure:

$$R_yR^1SiO_{(4-y)} \qquad \text{II}$$

in which R is as above, and y is 0, 1, 2 or 3. In addition, or alternatively, the organopolysiloxane can also contain, for example, organic groups such as acrylates, carbonates, polybutylenes or the like.

The reactive organopolysiloxane can also comprise mixtures or copolymers of the above organopolysiloxanes. Obviously, however, the organopolysiloxane must have at least one, preferably at least two, units of formula I for cross linking.

In a preferred embodiment of the invention, the reactive organopolysiloxane comprises a organopolysiloxane having the structure.

$$OH(Si(CH_3)_2))_zH \qquad \text{III}$$

wherein z is an integer of 3 to 10,000 or more.

The reactive organopolysiloxanes can have a wide variety of viscosities such as from about 10,000 cps and 400,000 cps at 25° C.

The acetoxysilane cross linking agent of the reactive organopolysiloxane of formula I comprises a material or a mixture of materials of the structure $$R^2_{4-a}SiR^3a$$

in which $R^2$ is a monovalent hydrocarbon group having up to 20 carbon atoms such as an alkyl (e.g., methyl, ethyl, propyl or butyl) or a phenyl group, $R^3$ is an acetoxy group, and a is 2, 3, or 4. In addition, the hydrolysis and condensation products of these silanes such as, for example, organopolysiloxanes containing the above acetoxy groups are also functional herein. Examples of specific acetoxysilanes include methyltriacetoxysilane, ethyltriacetoxysilane and mixtures thereof. The acetoxy cross linking agents are used in amounts of about 10 ppm to 10 wt % based on the weight of the organopolysiloxane. Preferably, the amount of cross linking agent is sufficient to provide a ratio of reactive groups on the organopolysiloxane to acetoxy groups of 0.1 to 10 and more preferably 0.5 to 2.

The metal catalysts suitable for use in the acetoxy curing reactive organopolysiloxane are known in the art and may include, for example, organic metal compounds such as organotin salts.

Examples of catalysts include stannous octoate, dibutyltin dilaurate, dibutyltin diacetate, dimethyltin dineodecanoate, dibutyltin dimethoxide, isobutyl tin triceroate, dimethyltin dibutyrate, dimethyltin dineodecanoate, triethyltin tartrate, tin oleate, tin naphthenate, tin butyrate, tin acetate, tin benzoate, tin sebacate, and tin succinate, platinum. Generally, these catalysts are used in amounts of between about 0.001 and 10 wt. % based on the weight of the composition. Platinum catalyst is preferred for the optically clear biofouling resistant compositions of the present invention specially formulated for very high light transmission.

In another embodiment, the curably reactive organopolysiloxane is a polydimethylsiloxane capped at both molecular terminals with dimethylvinylsiloxy groups, a methylvinylsiloxane.dimethylsiloxane copolymer capped at both molecular terminals with trimethylsiloxy groups, a methylvinylsiloxane.dimethylsiloxane copolymer capped at both molecular terminals with dimethylvinylsiloxy groups, a methylvinylsiloxane.dimethylsiloxane copolymer capped at both molecular terminals with dimethylvinylsiloxy groups, a methyl(3,3,3-trifluoropropyl)siloxane.dimethylsiloxane copolymer capped at both molecular terminals with dimethylvinylsiloxy groups, a polydimethylsiloxane capped at both molecular terminals with dimethylhexenylsiloxy groups, a methylhexenylsiloxane.dimethylsiloxane copolymer capped at both molecular terminals with trimethylsiloxy groups, a methylhexenylsiloxane.dimethylsiloxane copolymer capped at both molecular terminals with dimethylhexenylsiloxy groups, a methylphenylsiloxane.dimethylsiloxane copolymer capped at both molecular terminals with dimethylhexenylsiloxy groups, and a methyl(3,3,3-trifluoropropyl)siloxane.dimethylsiloxane copolymer capped at both molecular terminals with dimethylhexenylsiloxy groups.

A preferred cross linking agent is a polyorganosiloxane that contains at least two silicon-bonded hydrogen atoms in its molecule and can be represented by methyl, ethyl, propyl, and other alkyl groups; phenyl, tolyl, and other aryl groups; phenethyl or other univalent hydrocarbon groups represented by aralkyl groups; 3-chloropropyl group, 3,3,3-trifluoropropyl group, and other halogenated alkyl groups. Preferably, the cross linking agent is a polymethylhydrogensiloxane capped at both molecular terminals with trimethylsiloxy groups, a methylhydrogensiloxane.dimethylsiloxane copolymer capped at both molecular terminals with trimethylsiloxy groups, a cyclic methylhydrogensiloxane.dimethylsiloxane copolymer capped at both molecular terminals with dimethylhydrogensiloxy groups, a methylhydrogensiloxane.dimethylsiloxane copolymer, cyclic polymethylhydrogensiloxane, an organosiloxane copolymer consisting of siloxane units $R_3SiO_1/2$, siloxane units $R_2HSiO_1/2$, and siloxane units $SiO_4/2$, an organosiloxane copolymer consisting of siloxane units $R_2HSiO_1/2$ and siloxane units $SiO_4/2$, an organosiloxane copolymer consisting of siloxane units of formula $RHSiO_2/2$ and siloxane units of formula $RSiO_3/2$ or siloxane units of formula $HSiO_3/2$, or a mixture of two or more of these polyorganosiloxanes. R is a univalent saturated hydrocarbon group or a halogenated alkyl group. Preferably, the amount of cross linking agent is sufficient to provide a ratio of reactive groups on the organopolysiloxane to hydrogen atoms on the cross linking agent of 0.1 to 10 and more preferably 0.5 to 2.

In a preferred embodiment, the curably reactive organopolysiloxane is a vinyl-terminated PDMS, which can be synthesized by the reaction of commercial hydroxyl-terminated PDMS with dimethylvinylchlorosilane to yield compounds of the following chemical formula

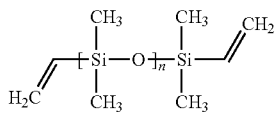

The vinyl groups in the above PDMS polymer can copolymerize with vinyltrialkyloxysilane, and can also take part in a cross-linking reaction with 1,3-divinyltetramethyldi siloxane.

The fouling resistant composition of the present invention may also comprise rheological control and reinforcing fillers. Such fillers are known in the art and generally comprise those conventionally found in silicone elastomers. They include, for example, precipitated or fumed silicas which may be pre-treated or treated in situ to render them hydrophobic. These control viscosity, thixotropy, flow, sag resistance, and sedimentation and have surfaces comprising siloxane and silanol functionalities. The viscosity of the silicone resin is preferably adjusted such that a uniform coating results with a thickness of between 2/1000 and 10/10000 of an inch.

Preferably, for the optically clear biofouling resistant compositions of the present invention specially formulated for very high light transmission, the filler comprises nanoparticles of amorphous fumed silica having a primary particle size between 5 to 150 nanometer (nm) with 50-800 $m^2/g$ surface area, preferably 120-200 $m^2/g$, untreated or treated with silanes (e.g. trimethylchlorosilane), silazane (e.g. hexamethyldisilazane) or low molecular weight organopolysiloxane such as organoalkoxysilane, organochlorosilane, organosilazane, or other organic silicon compound and mixtures thereof. In dimethylsiloxane, dimethylyvinyl-terminated anti fouling compositions, dimethylyvinylated and trimethylated silica may be used. In dimethylsiloxane, hydroxyl terminated anti fouling compositions, untreated amorphous fumed silica may be used.

Examples of fumed silica (modified or unmodified) include, but are not limited to, Bindzil® 215 (anionic surface), Bindzil® 15/500 (anionic surface), Bindzil® 30/360 (anionic surface), Bindzil® 830 (anionic surface), Bindzil® 2034 DI (anionic, acid surface), Bindzil® 9950 (anionic surface), Bindzil® 50/80 (anionic surface), Bindzil® CAT80 (cationic surface), Bindzil® CC30 (silane treated surface) and Cabosil R. Preferably, hydrophobic fumed silica is used by treating the surface of hydrophilic fumed silica such as Aerosil® to render it water repellent. Degussa's Aerosil® P202 is treated with polymethylsiloxane (silicone oil) and Aerosil® R805 is treated with trimethoxyoctylsilane.

Generally, more dispersing energy is needed to disperse a given amount of silica as the surface area increases. In other words, silicas with lower surface area are easier to disperse. In a fully dispersed system, lower surface area silicas require a higher weight loading in the resin than those of higher surface area to achieve similar viscosities and behaviors. Viscosity can be measured by use of commonly available viscometers.

The fillers are used in an amount sufficient to provide the desired properties. Generally, this is an amount of about 0.1 to 70 parts per hundred parts of the organopolysiloxane, preferably ranging from about 5 wt % to about 70 wt % of the organopolysiloxane or about 7 wt % to about 35 wt % or about 7 wt % to about 15.0 wt % or about 30 wt % to about 60 wt %. The amount added depends on the resin chemistry and molecular weight distribution, dispersion condition (intensity, equipment) and nature of other additives used in formulating the antibiofouling composition.

Particle size distributions of the amorphous fumed silica nanoparticles may fall anywhere within the range from about 1 nm, or less, to less than about 400 nm, alternatively from about 2 nm to less than about 300 nm, alternatively from about 5 nm to less than about 150 nm, alternatively 1 nm to 100 nm, alternatively 5 nm and 50 nm, alternatively 1 nm and 25 nm, and alternatively 1 nm and 10 nm.

Fumed silicas should be incorporated based on individual formulation needs and experience. Typical application methods suggest that the silica can be incorporated early into the base resin to increase the viscosity of the system. This increase in viscosity results in an increase of the shear forces that are needed for proper dispersion of the silica into the formulation. In many cases, the mixture is sheared until a specific, desired "grind"—as an indication of the extent of dispersion—is achieved. At this point, the other additives, as well as any required reactive diluent, can be added. The actual method of incorporation may vary depending on the specific formulation, dispersing equipment, and customer specificity. Grindometer readings of <50 μm are generally preferred, which indicates nearly complete dispersion. Grindometer readings of 15-40 μm will give best anti-settling, anti-sag, clarity, and stability.

In order to boost the strength, viscosity and improve the long-term stability of antibiofouling coating compositions, additives at a concentration of 7-30% by weight of fumed silica may be added. Such additives can comprise glycols and non-ionic surfactants of various molecular weights, which can range from simple ethylene glycol to larger propylene glycols with molecular weights of 750. The actual materials and the amounts used are a function of both formulation and customer specifications. The mechanism by which the additives function depends on the particular material used. Glycerin, glycol, and other polyhydroxyl compounds have multiple hydrogen bonding sites which allow them to act as "bridging agents" between fumed silica aggregates. This bridging strengthens the silica network, resulting in increased viscosity.

In another embodiment, resin fillers in addition to fumed silica or in lieu of fumed silica may be used for material strength and rheological control. Resin fillers are short chain silicone polymers such as short chain polymethylsilsesquioxane that are soluble in the fouling release silicone composition itself. They have the best optical properties but at the sacrifice of the final silicone's products strength and durability.

The biofouling resistant coating of the present invention may contain a curing catalyst in an amount sufficient for cross-linking and curing.

In one embodiment, the curing catalyst comprises organic peroxides such as 2,5 dimethyl-2.5 di(t-butylperoxy) hexane, 2,4 dichloro-benzoyl peroxide, or dicumyl peroxide for peroxide initiated cure.

Preferably, a platinum group metal catalyst such as ruthenium, rhodium, palladium, osmium, iridium, or platinum per se, or compounds of these metals that possess a catalytic activity with regard to the curing reaction, such as platinum on a fine-powdered silica carrier, chloroplatinic acid, an alcohol solution of a chloroplatinic acid, a platinum-olefin complex, a divinyl-tetramethyldisiloxane complex of a chloroplatinic acid, a divinyl-tetramethyldisiloxane complex of platinum, and thermoplastic resin powders that contain platinum-group metals. Preferably, the catalyst should be used in a catalytic amount. A preferred catalytic amount is 0.1 to 1,000 ppm of the pure metal contained the catayst per total amount of curably reactive organopolysiloxane.

If desired, the antibiofouiling composition of the present invention may contain additional optically clear ingredients such as diluents, extenders, for example silicone fluids, silicone resins, stabilizers, or surfactants, biocides, and processing aids such as cyclic or linear polydiorganosiloxanes. One embodiment comprising dimethylsiloxane, dimethylvinyl terminated based antibiofouiling composition, further comprises up to 35 wt % vinyl containing resin (polyalkylakenylsiloxane) $Vi[(CH_3)_2SiO]n\ Si(CH_3)_2Vi$.

One particularly advantageous optional ingredient in the formulation of the present invention is a diluent. Such diluents are often necessary to decrease the viscosity of the silicones sufficiently to permit application.

Examples of diluents include silicon containing materials such as hexamethyldisiloxane, octamethyltrisiloxane, and other short chain linear siloxanes, cyclic siloxanes such as octamethylcyclotetrasiloxane and decamethylcyclopentasiloxane, organic materials such as alkanes and alkenes, including ethylbenzene, xylene, benzene, toluene, alcohol, mineral spirit, acetone, tetrahydrofuran, mehtylethylketone, methylisobutylketone or any other material or mixture of materials which can dilute the formulation without affecting any of the components of the formulation.

One embodiment of the antibiofouiling coating composition of the present invention comprises 40-70 Wt % dimethyl, methylhydrogen siloxane; 15-40% dimethly siloxane, dimethylvinyl-terminated; 10-30 wt % dimethylvinylated and trimethylated silica; 1.0-5.0 tetramethyl tetravinyl cyclotetrasiloxane; less than 1 wt % ethylbenzene, 0.5 wt % xylene, and a catalytic amount of platinum.

Another embodiment of the antibiofouiling coating composition of the present invention comprises 60-90 wt % vinylpolydimenthylsiloxane; 10-30% vinly containing resin (ployalkylalkenylsiloxane); 0.0001 benzene; 0.0001 toluene and a catalytic amount of platinum.

Another embodiment of the antibiofouiling coating composition of the present invention comprises about 60-80 wt % dimethylsoloxane, hydroxy-terminated; 7.0-13.0 wt % amorphous fumed silica; 1.0-5.0 wt % ethyltriacetoxysilane; 1.0-5.0 wt % methyltriacetoxysilane. Suitable additives for this embodiment include at least one of tetramethoxysilane, tetraethoxysilane, dimethyldimethoxysilane, methylphenyldimethoxysilane, methylphenyldiethoxysiolane, phenyltrimethoxysilane, methyltrimethoxy silane, methyltriethoxysilane, vinyltrimethoxysilane, allyltrimethoxysilane, ally ltriethoxy silane, or other alkoxysilanes.

To improve the adhesive properties of the antibiofouiling composition, the composition may be combined with an adhesion promoter. Adhesion promoter is exemplified by silane coupling agents such as 3-methacryloxypropyltrimethoxy silane, 3-acryloxypropyl trimethoxysilane, or similar organoalkoxysilanes that contains an acryloxy group; 3-aminopropyltrimethoxysilane, 3-(2-aminoethyl)-aminopropyl trimethoxysilane, or similar organoalkoxysilanes that contains an amino group; 3-glycidoxypropyltrimethoxysilane, similar organoalkoxysilanes that contains an epoxy group, or condensation-reaction products such as a condensation reaction product between 3-glycidoxypropyltrialkoxy silane and a silanol-endcapped dimethyloligosiloxane, a condensation reaction product between 3-glycidoxypropyltrialkoxysilane and a silanol-endcapped methylvinyloligosiloxane, and a product of a condensation reaction between 3-glycidoxypropyltrialkoxysilane and a silanol-endcapped dimethylsiloxane-methylvinylsiloxane copolymer and mixtures thereof. The adhesion promoters can be used in an amount of 0.1 to 10 parts by weight, preferably 0.1 to 5 parts by weight, per 100 parts by weight of the sum of the PDMS resin.

In another embodiment, the adhesion promoter may contain a mixture of organic and inorganic compounds. Dow Corning DC5200 for instance comprises 60.0-85 wt % Octamethyltrisiloxane, 5.0-10.0 wt % 1-Methoxyisopropyl orthosilicate, 5.0-10.0 Tetrapropyl orthosilicate, and 3.0-7.0 Tetrabutyl titanate.

In another embodiment, a primer or tie coat polymer capable of forming an intimate covalent bond matrix with the instrument housing and/or sensor surface is applied prior to applying the PDMS based antibiofouiling coating composition of the present invention. Commercial available tie coat resins may be used. U.S. Pat. No. 5,449,553 and U.S. Pat. No. 5,593,732, US Published Application No. 20080138634 disclose tie coat composition and are herein incorporated by reference. Suitable tie coats may have viscosity of from about 400 to about 400,000 centipoise at about 25° C.; preferably about 100,000 to about 300,000 centipoise at 25° C.; and more preferably, about 95,000 to about 150,000 centipoise at 25° C.

In one embodiment, the tie coat is bonded to the substrate and the PDMS optically clear fouling release coating of the present invention through silicone cross linking between the tie coat and fouling release coat. This bond is covalent in nature and results in a transmission of toughness to the fouling release coat from the tie coat and allows the entire system to achieve a very strong toughness. Commercially available silicone based tie coats include SS4179 (GE/MOMENTIVE), SS4044 (GE/MOMENTIVE), SS4004 (GE/MOMENTIVE). As used in this description, tie coat encompasses primers, epoxy resins, and barrier coats or any pre-antifoulant coat layer.

In another embodiment, a clear epoxy adhesive is first applied to the substrate optionally followed by a tie coat layer prior to applying the PDMS based antibiofouiling composition of the present invention. The epoxy adhesive preferably comprises a polymer blend containing silane coupling agent having primary or secondary amines and adheres strongly to both similar and dissimilar materials including metals, glass, ceramics, vulcanized rubbers and many plastics. One preferred epoxy resin is a polyamine/polyamide blend comprising 65-70 Wt % Bisphenol a—epichlorohydrin polymer; 30-35 wt % Alkyl (c12-14) glycidyl ether; diluent n-Butyl glycidyl ether; and fatty acids, C18-unsatd., dimers, reaction products with polyethylenepolyamines (Polyamide Resin) Another preferred epoxy resin comprises Polyoxypropylenediamine 25-50%; Reaction products of isophorone diamine with phenol/formaldehyde 10-25%; Isophoronediamine 10-25%; Reaction products of benzene-1,3-dimethaneamine with hydroxybenzene and formaldehyde 10-25%; Hydroxybenzene 5-12% and m-Xylene diamine 5-12%. And yet another preferred epoxy resin comprises Bisphenol-A type epoxy resin 50-70%; Benzyl alcohol 10-20% Bisphenol-F type epoxy resin 10-20%; Ethylene glycol monobutyl ether 0.1-0.3% U.S. Pat. No. 6,391,464, entitled Epoxy Coatings and Surfaces Coated Therewith disclose other epoxy coating compositions and is herein incorporated by reference.

In another embodiment, the barrier coat or tie coat preferably comprises polyurethane adhesives or other suitable barrier coats used in the art. The adhesives suitable according to the invention are one-component polyurethane adhesives or two-component polyurethane adhesives. The adhesives may be liquid, but they may also be hot-melt adhesives. The adhesives may contain solvent, but they are preferably solvent-free. Crosslinking of the polyurethane adhesives suitable according to the invention is based on the reaction of reactive NCO groups, in particular aromatic NCO groups, with H-acidic functional groups, for example OH groups, amino groups or carboxyl groups. An alternative crosslinking method involves the reaction of the NCO groups with moisture from the applied adhesive, the substrate or the surroundings with formation of urea groups. These crosslinking reactions are known and they may also proceed concurrently. The adhesives conventionally contain catalysts, for example amine or tin catalysts, to accelerate such reactions.

Known coating material or adhesive polyisocyanates may be used such as polyisocyanates having two or more isocyanate groups. Suitable polyisocyanates are for example 1,5-naphthylene diisocyanate (NDI), 2,4- or 4,4'-diphenylmethane diisocyanate (MDI), hydrogenated MDI (H12MDI), xylylene diisocyanate (XDI), tetramethylxylylene diisocyanate (TMXDI), di- and tetraalkylene diphenylmethane diisocyanate, 4,4'-dibenzyl diisocyanate, 1,3- or 1,4-phenylene diisocyanate, tolylene diisocyanate (TDI), 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane (IPDI), tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, methylene triphenyl triisocyanate (MIT), phthalic acid bis-isocyanatoethyl ester, trimethylhexamethylene diisocyanate, 1,4-diisocyanatobutane, 1,12-diisocyanatododecane and dimer fatty acid diisocyanate.

Suitable at least trifunctional isocyanates are polyisocyanates which are obtained by trimerization or oligomerization of diisocyanates or by reaction of diisocyanates with low molecular weight polyfunctional compounds containing hydroxyl or amino groups.

Commercially obtainable examples are trimerization products of the isocyanates HDI, MDI or IPDI or adducts of diisocyanates and low molecular weight triols, such as trimethylolpropane or glycerol.

In another embodiment, silane-functional polyurethanes may be used as moisture-curing adhesives and sealants. These silane-functional polyurethanes contain silane groups as reactive groups and are typically prepared by the reaction of aminosilanes with polyurethane prepolymers containing isocyanate groups. EP-A-0 202 491 mentions silane-functionalized polyester melt adhesives in which an adduct of a polyester polyol and a diisocyanate is reacted with an amino- or mercaptosilane, or an adduct of an amino- or mercaptosilane and a diisocyanate is reacted with a polyester polyol. EP-A-0 371 370 discloses melt adhesives which aftercrosslink on exposure to moisture and contain terminal alkoxysilane and/or NCO groups. EP-A-0 371 370 further discloses that these alkoxysilane end groups can be introduced via mercaptosilane or via a series of aminosilanes.

It is conventional to use low molecular weight isocyanates in the synthesis of polyurethane adhesives. For chemical reasons, it is impossible to prevent small proportions of monomeric isocyanates from also being present in the adhesive. In a further group of polyurethane adhesives, oligomeric isocyanates are added to the adhesive to improve specific characteristics. These are intended to react with crosslinking agents, for example polyols, or with water, in order to yield a crosslinked adhesive.

Prior to applying the tie coat or epoxy resin, all bonding surfaces are carefully cleaned, degreased and dried to obtain maximum bond strength. Also, when bonding to certain metal surfaces, vulcanized rubbers, etc., chemical etching may be employed for optimal adhesion and environmental durability. Non-porous surfaces may be roughened with sandpaper or emery paper for hard materials. Where appropriate, air plasma or corona treatment is applied to the surface to be coated to improve the characteristics of the materials by raising surface energy (dyne level). Commercially available corona treatment equipments may be used.

Mixing of the components of the invention causes curing in the presence of adequate moisture or heat. As such, the components are often stored in separate containers prior to use or they are mixed and stored in containers which exclude moisture. For instance, one container could contain the catalyst and a second could contain the reactive organopolysiloxane and the cross linking agent. Alternatively, the catalyst could be mixed with the reactive organopolysiloxane in one container and the cross linking agent could be in a second container. The filler and optional ingredients could be included in either or both of the parts depending on factors such as stability, viscosity, and interactions.

Curable bioresistant composition is prepared by uniformly mixing the curably reactive organopolysiloxane and the cross linking agent with addition of other optional components. The composition can be prepared in a commercial mixer such as a Ross mixer, planetary mixer, or Hobart mixer.

The composition of the present invention is then mixed and applied to the marine instrument housing and sensor elements. The method of applying can be, but is not limited to, dip coating, spray coating or flow coating. For example, they can be deposited via an electrodeposition technique such as electroplating, electrophoretic deposition, or electrobrushing.

The diluent, if used, is then allowed to evaporate leaving the cured composition. If desired, the coated device can be heated or radiated to facilitate the cure. Heating can be at temperatures of 50° C. to 120° C. for several minutes up to several hours, depending on the heat stability of the substrate.

The resultant device has a thin, adherent silicone coating which renders it biofouling resistant. The coating can have a variety of thicknesses such as from about several nanometers up to several millimeters, preferably 2/1000 to 10/10000 of an inch.

In order that the invention may become more clear there now follows examples which are illustrative of the invention. Unless indicated, all parts are by weight and all viscosities are at 25° C.

One embodiment of the invention is one in which the composition and method of the present invention is used in conjunction with other biofouling resistant methodologies known in the art. For instance, in conjunction with mechanical wiper system, the composition and method of the present invention will result in a more effective cleaning of the coated sensor and/or housing. In another embodiment, the composition of the present invention further comprises organic compounds having antibiofoulant properties selected from compounds consisting of algaecides, herbicides, bactericides, and pesticides as well natural product antibiofoulants such as capsaicin and zosteric acid. Mixtures of two or more antibiofoulants can be used.

Preferred anti foulants are those compounds that are stable at processing conditions and that do not excessively decrease transmission of light through the cured composition or damage the compositions' physical and mechanical properties. It is anticipated that the antibiofoulants will diffuse over time to the surface of a coating composition and leach out of the coat. Diffusion through the biofouling resistant coating will provide a long-lived protective coating.

The anti fouling agents must be chosen and incorporated so that they do not excessively decrease transmission of light through the organopolysiloxane polymer. This normally means that they must form a solid solution in the polymer, as opposed to a suspension. Common anti-biofoulants include, but are not limited to algaecides, herbicides, bactericides, and pesticides. These materials may be synthesized (e.g. urea-based algaecides, glyphosates (herbicide), fluoroquinolones (bactericide), copper oxides, etc.), or they may be naturally occurring (e.g., capsaicin, zosteric acid, etc.). The antibiofoulants must be stable at the processing conditions of the polymer. Preferred antibiofoulants are not expected to form bound complexes with the coating composition. The final product preferably has optical transparency greater than 70%, good adhesion, the ability to inhibit biological fouling, and a low leach rate of the antibiofoulants into the environment.

Transmission spectra may be determined in any suitable manner in the art such as by the use of a UV-Visible spectrometer using a 600 groove/mm grating with a 300 nm blaze wavelength and 25 μm slit. The "percent transmission" or amount of light allowed to pass through the polymer samples over a spectral range of 400 to 850 nm is determined. 100% transmission is effectively passing all of the tested wavelengths of light through the sample. Preferably, the optically clear antibiofouiling composition of the present invention has an index of refraction above 1.40, most preferably within the range of 1.45 to 1.56 at 25° C.

Example 1

For the case of instrument housings, gliders and similar platforms, special care is taken to coat the areas where sections of housing are joined together with o-ring connections or have installed end caps with o-ring sections. FIG. 1 illustrates biofouling in o-ring jointed seams 10 of multi-component instrument housing 20. In order to protect these areas from biofouling settlement and to ensure that the applied fouling release coating does not flow into the o-ring sealed area where it could disrupt the sealing mechanism, the following method of coating is implemented. A layer of clear plastic tape is applied to cover the o-ring bearing seams joining two pieces of the instrument housing. To equalize the pressure across the tape, a hole or holes is made on the tape. The anti-fouling coating is then applied over the tape in accordance with the teachings of the present invention. The circular circumference, joining two pieces of the instrument housing as described have a layer of clear plastic tape applied. The coating is then applied over the tape.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. Documents including patents and non patent references cited herein are expressly incorporated by reference.

While illustrative embodiments have been illustrated and described, it will be appreciated that various changes can be made therein without departing from the spirit and scope of the invention.

The embodiments of the invention in which an exclusive property or privilege is claimed are defined as follows:

1. An optically clear biofouling-resistant coating on a substrate used for submerged marine applications, the optically clear biofouling-resistant coating comprising:
 an optically clear tie coat on the substrate used for submerged marine applications; and
 an optically clear biofouling-resistant composition comprising a curably reactive organopolysiloxane having at least one terminal reactive functional group, at least one silicon bonded organic group, and an organopolysiloxane cross linking agent; wherein said terminal reactive group is a hydroxyl group, an alkoxy group, an aryloxy group, an amino group, an amido group, a halogen, or a vinyl group; and said silicon bonded organic group is a methyl group, an ethyl group, a vinyl group, a haloalkyl group, or a phenyl group;
 wherein the optically clear biofouling-resistant coating has greater than 50% light transmission of wavelengths between 400 nm and 800 nm, and wherein the optically clear biofouling-resistant coating has a refractive index of 1.30 to 1.56.

2. The optically clear biofouling-resistant coating of claim 1, wherein the optically clear tie coat comprises a polymer selected from the group of an epoxy, a polyurethane, and a combination thereof.

3. The optically clear biofouling-resistant coating of claim 1, wherein the optically clear tie coat comprises a silane coupling agent.

4. The optically clear biofouling-resistant coating of claim 1, wherein the substrate is selected from the group consisting of aluminum, titanium, stainless steel, copper nickel, glass, polyurethane, polyvinyl chloride, ceramic, poly acetyl, fiberglass reinforced plastic, carbon fiber reinforced plastic, thermoplastics, thermosets, and combinations thereof.

5. The optically clear biofouling-resistant coating of claim 1, wherein the substrate is a marine instrument selected from the group consisting of an acoustic sensor, an optical sensor, an electrode, electromagnetic sensors, and strain gauge devices.

6. The optically clear biofouling-resistant coating of claim 1, wherein the substrate includes a serial number or other identification marking that is visible through the optically clear biofouling-resistant coating.

7. The optically clear biofouling-resistant coating of claim 1, wherein the optically clear tie coat is a primer capable of forming an intimate covalent bond matrix with the substrate.

8. The optically clear biofouling-resistant coating of claim 1, wherein the optically clear biofouling-resistant coating has greater than 70% light transmission of wavelengths between 400 nm and 800 nm.

9. The optically clear biofouling-resistant coating of claim 1, wherein the optically clear biofouling-resistant composition further comprises an antifoulant selected from the group consisting of algaecides, herbicides, bactericides, pesticides, capsaicin, zosteric acid, and combinations thereof.

10. An optically clear biofouling-resistant coating on a substrate used for submerged marine applications, the optically clear biofouling-resistant coating comprising:
    an optically clear adhesive layer on the substrate;
    an optically clear biofouling-resistant composition comprising a curably reactive organopolysiloxane having at least one terminal reactive functional group, at least one silicon bonded organic group, and an organopolysiloxane cross linking agent; wherein said terminal reactive group is a hydroxyl group, an alkoxy group, an aryloxy group, an amino group, an amido group, a halogen, or a vinyl group; and said silicon bonded organic group is a methyl group, an ethyl group, a vinyl group, a haloalkyl group, or a phenyl group; and
    an optically clear tie coat between the adhesive layer and the optically clear biofouling-resistant composition;
    wherein the optically clear biofouling-resistant coating has greater than 50% light transmission of wavelengths between 400 nm and 800 nm, and wherein the optically clear biofouling-resistant coating has a refractive index of 1.30 to 1.56.

11. The optically clear biofouling-resistant coating of claim 10, wherein the optically clear adhesive layer comprises an epoxy polymer.

12. The optically clear biofouling-resistant coating of claim 10, wherein the optically clear tie coat comprises a polymer selected from the group of an epoxy, a polyurethane, and a combination thereof.

13. The optically clear biofouling-resistant coating of claim 10, further comprising a silane coupling agent in one or more of the optically clear adhesive layer, the optically clear tie coat, and the optically clear biofouling-resistant composition.

14. The optically clear biofouling-resistant coating of claim 10, wherein the substrate is selected from the group consisting of aluminum, titanium, stainless steel, copper nickel, glass, polyurethane, polyvinyl chloride, ceramic, poly acetyl, fiberglass reinforced plastic, carbon fiber reinforced plastic, thermoplastics, thermosets, and combinations thereof.

15. The optically clear biofouling-resistant coating of claim 10, wherein the substrate includes a serial number or other identification marking that is visible through the optically clear biofouling-resistant coating.

16. The optically clear biofouling-resistant coating of claim 10, wherein the substrate is a marine instrument selected from the group consisting of an acoustic sensor, an optical sensor, an electrode, electromagnetic sensors, and strain gauge devices.

17. The optically clear biofouling-resistant coating of claim 10, wherein the optically clear biofouling-resistant coating has greater than 70% light transmission of wavelengths between 400 nm and 800 nm.

18. The optically clear biofouling-resistant coating of claim 10, wherein the optically clear biofouling-resistant composition further comprises an antifoulant selected from the group consisting of algaecides, herbicides, bactericides, pesticides, capsaicin, zosteric acid, and combinations thereof.

* * * * *